United States Patent [19]

Yeh

[11] Patent Number: 5,192,211
[45] Date of Patent: Mar. 9, 1993

[54] METHOD OF MAKING ANIMAL SPECIMEN

[76] Inventor: Tzuoo-Lie Yeh, No. 23, tzu Li Li, Chung Li City, Taiwan

[21] Appl. No.: 737,011

[22] Filed: Jul. 29, 1991

[51] Int. Cl.$^5$ .............................................. G09B 23/00
[52] U.S. Cl. ..................................... 434/296; 434/295; 424/75
[58] Field of Search ................ 434/295, 296; 8/94.11, 8/94.15; 424/75, 659

[56] References Cited

U.S. PATENT DOCUMENTS

| | | | |
|---|---|---|---|
| 1,495,196 | 5/1924 | Oakley | 424/75 |
| 1,602,489 | 10/1926 | Hochstetter | 434/295 X |
| 2,219,927 | 10/1940 | Jones | 424/75 |
| 3,057,775 | 10/1962 | Rendon | 424/75 |
| 3,264,182 | 8/1966 | Langner | 424/75 |
| 3,780,452 | 12/1973 | Jackson | 434/296 |

FOREIGN PATENT DOCUMENTS 364329 1/1932 United Kingdom ................ 434/296

*Primary Examiner*—Richard J. Apley
*Assistant Examiner*—Karen A. Jalbert
*Attorney, Agent, or Firm*—W. Wayne Liauh

[57] ABSTRACT

A method of making animal specimen, of which the processing steps include a dead animal as a specimen body to be directly soaked in a 3-in-one mixed liquid for a given period of time; the 3-in-one mixed liquid comprises granular boric acid, NaCl, phenol, a liquid of formaldehyde solution, and a volatile alcohol. A specimen body soaked with such a mixed liquid has an excellent antiseptic result without removing the muscles, bones and internal organs of a specimen body, but a specimen body can be dried and made simply.

3 Claims, No Drawings

METHOD OF MAKING ANIMAL SPECIMEN

BACKGROUND OF THE INVENTION

According to the conventional method, an animal specimen can be made by removing an animal's muscles, bones, and internal organs; then, the skin with hairs or furs of the animal is further processed to restore its original vivid shape and natural color of the animal. In the conventional steps of making an animal specimen, the skin peeling and filling steps are quite complicated, and such steps have to be processed by a professional person or persons in addition to using tools and chemicals; therefore, the conventional method is deemed rather expensive.

SUMMARY OF THE INVENTION

This invention relates to a new method of making animal specimen without using the steps of peeling skin, and removing muscles, bones and the internal organs.

The prime feature of the present invention is to provide a method of making animal specimen by means of a special antiseptic liquid, which can directly infiltrate into a specimen to have the steps of making a specimen much simplified.

Another feature of the present invention is to provide a method whereby a specimen can be made with a natural color and an elasticity without removing the bones and the internal organs from an animal so as to facilitate further study later on.

DETAILED DESCRIPTION

The method and process of making a specimen according to the present invention are described as follows:

The liquid for making specimen according to the present invention is prescribed with the following three substances, i.e.,

| A. | Boric acid | 100%-10 g | in mixed granular |
| | NaCl | -150 g | condition; |
| | Phenol | -30 g | |
| B. | Formaldehyde solution | 35%-5L; | |
| C. | Volatile alcohol | 98%-5L. | |

To mix up the aforesaid three kinds of chemicals, first pour chemical "B" (Formaldehyde solution) into a container filled with chemical "C" (volatile alcohol); then, pour slowly chemical "A" (Boric acid; NaCl; and Phenol) into the same container. Wait for ten minutes upon the pouring operation being completed, and then agitate the chemicals till being dissolved completely. The mixed liquid is ready for making specimen; the liquid may be called 3-in-one mixed liquid.

A specimen body has to be cleaned and washed, and weighed first; one kg of specimen body has to be soaked in the 3-in one mixed liquid for 36 hours; in other words, the time for soaking a specimen body may be figured out by using the aforesaid requirement. as soon as a soaking time required for a given specimen body is up, the specimen body can be removed from the mixed liquid for further processing, and then a specimen is completed.

A specimen made with the method according to the present invention would have an excellent antiseptic result so as to maintain the specimen in its natural color and elasticity. The present invention is deemed a new and valuable method in making a specimen and in the industrial field as well.

I claim:

1. A method for making animal specimen capable of maintaining its natural color and elasticity, said method comprising the steps of:
   (a) preparing a 3-in-one mixed liquid solution by adding, per 10 liters of said 3-in-one mixed liquid solution, 5 liters of 35% formaldehyde into 5 liters of volatile alcohol to form an intermediate mixed solution, then adding a granular mixture containing 10 grams of 100% boric acid, 150 grams of sodium chloride and 30 grams of phenol into said intermediate mixed solution to form said 3-in-one mixed liquid solution, and agitating said 3-in-one mixed liquid solution until said granular mixture is completely dissolved;
   (b) cleaning and washing said specimen to be treated;
   (c) soaking said specimen in said 3-in-one mixed liquid solution; and
   (d) removing said specimen from said 3-in-one mixed liquid solution.

2. The method of making animal specimen of claim 1 wherein said volatile alcohol is 98% alcohol.

3. The method of making animal specimen of claim 1 wherein said specimen is soaked in said 3-in-one mixed liquid solution for a duration of 36 hours per kilogram of the weight of said specimen.

* * * * *